United States Patent
Yamagishi et al.

(10) Patent No.: US 6,491,898 B1
(45) Date of Patent: Dec. 10, 2002

(54) TOOTH COATING COMPOSITION

(75) Inventors: Atsushi Yamagishi, Tokyo; Yukihiro Nakano, Wakayama, both of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/508,113

(22) PCT Filed: Sep. 4, 1998

(86) PCT No.: PCT/JP98/03976

§ 371 (c)(1),
(2), (4) Date: Mar. 20, 2000

(87) PCT Pub. No.: WO99/15131

PCT Pub. Date: Apr. 1, 1999

(51) Int. Cl.⁷ .............................. A61K 7/16; A61K 7/22; A61K 31/74; A61K 31/785; A61K 31/14
(52) U.S. Cl. ...................... 424/49; 424/54; 424/78.18; 424/78.23; 424/78.24; 514/643
(58) Field of Search ...................... 514/54, 643; 424/49, 424/54, 78.18, 78.21, 79

(56) References Cited

U.S. PATENT DOCUMENTS 3,956,480 A * 5/1976 Dichter et al. ................ 424/54
6,048,913 A * 4/2000 Yamagishi et al. ......... 523/118

FOREIGN PATENT DOCUMENTS

| JP | 5-85915 | * | 4/1993 |
| JP | 6-279226 | * | 10/1994 |
| JP | 9-151123 | * | 6/1997 |
| JP | 9-202718 | * | 8/1997 |
| WO | WO 98/26749 | * | 6/1998 |

* cited by examiner

Primary Examiner—Frederick Krass
Assistant Examiner—Donna Jagoe
(74) Attorney, Agent, or Firm—Oblon, Spivak, McClelland, Maier & Neustadt, P.C.

(57) ABSTRACT

The invention relates to a tooth coating composition comprising (A) a polymer having one or more carboxyl or carbonyloxycarbonyl groups in its molecule, a weight average molecular weight of 10,000 to 5,000,000, a solubility of 1 g or higher in 100 g of absolute ethanol at 20° C. and a solubility of 10 g or lower in 100 g of water at 20° C., and (B) water or an alcohol having 1 to 5 carbon atoms. When coating teeth with the composition, the coating is not easily peeled by eating and drinking, but can be easily removed if necessary.

15 Claims, No Drawings

TOOTH COATING COMPOSITION

TECHNICAL FIELD

The present invention relates to a tooth coating composition.

BACKGROUND ART

The makeup of teeth is generally conducted by applying a composition containing a dye or pigment to the teeth.

For example, dental adhesives and the like have been known as means for applying such a composition to the teeth. These means are such that a monomer is applied to the teeth and polymerized in a short period of time by irradiation of ultraviolet light or heating for the purpose of enhancing the adhesive strength so as to keep the coating over a long period of time (for example, Japanese Patent Application Laid-Open Nos. 69494/1978 and 113089/1977).

On the other hand, the makeup of teeth requires such moderate adhesive strength that the coating is not easily peeled by eating and drinking, but can be easily removed if necessary. However, the application by the above-described dental adhesive is difficult to control the adhesive strength and the degree of application.

Accordingly, it is an object of the present invention to provide a tooth coating composition having such moderate adhesive strength that the coating is not easily peeled by eating and drinking, but can be easily removed if necessary.

DISCLOSURE OF THE INVENTION

The present inventors have found that a tooth coating composition comprising a film-forming polymer containing at least one carboxyl group or the like and having respective specific solubilities in water and ethanol, and water or/and a lower alcohol has moderate adhesive strength.

According to the present invention, there is thus provided a teeth coating composition comprising (A) a polymer having one or more carboxyl (—COOH) or carbonyloxycarbonyl (—COOCO—) groups in its molecule, a weight average molecular weight of 10,000 to 5,000,000, a solubility of 1 g or higher in 100 g of absolute ethanol at 20° C. and a solubility of 10 g or lower in 100 g of water at 20° C., and (B) water or an alcohol having 1 to 5 carbon atoms.

According to the present invention, there is also provided a method for coating teeth, which comprises applying the tooth coating composition described above to teeth.

According to the present invention, there is further provided use of the polymer (A) described above for coating teeth.

BEST MODE FOR CARRYING OUT THE INVENTION

The polymer (A) useful in the practice of the present invention has one or more carboxyl or carbonyloxycarbonyl groups in its molecule, and is preferably a polymer having, as a main chain, a chain obtained by polymerizing polymerizable vinyl group, and one or more carboxyl or carbonyloxycarbonyl groups at its side chains.

The side chain of the polymer (A) may have any other group than the carboxyl or carbonyloxycarbonyl group, and may have any other group than a phosphoric acid residue, for example, a sulfonic, hydroxyl or amide group.

Examples of the polymer (A) include homopolymers and copolymers having a structural unit represented by the following formula (1):

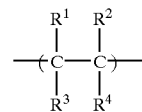

wherein $R^1$ and $R^2$ are the same or different from each other and are independently a hydrogen or halogen atom or a hydrocarbon group which may be substituted by a halogen atom, and at least one of $R^3$ and $R^4$ are the same or different from each other and are independently a group substituted by a carboxyl or carbonyloxycarbonyl group through an organic group, and the other group is a hydrogen or halogen atom or a hydrocarbon group which may be substituted by a halogen atom, with the proviso that $R^3$ and $R^4$ may form together a carbonyloxycarbonyl group.

Preferable examples of the polymer (A) include homopolymers and copolymers having a structural unit represented by the following formula (2):

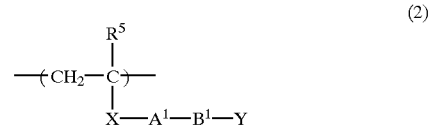

wherein $R^5$ is a hydrogen atom or a hydrocarbon group which may be substituted by a halogen atom, X is —COO— or —CON($R^6$)—, in which $R^6$ is a hydrogen atom or an alkyl group, $A^1$ is a single bond or a hydrocarbon group which may be substituted by a halogen atom, $B^1$ is a single bond, —OCO—, —COO—, —O—, —NHCO— or —CONH—, or may represent a polyalkyleneoxy or poly(alkyleneoxy)carbonyl group together with $A^1$, and Y is a hydrogen atom, a carboxyl group, an aryl group substituted by 1 to 3 carboxyl groups, an alkyl or alkenyl group substituted by 1 or 2 carboxyl groups, or a carbonyloxycarbonyl-substituted aryl group.

In the formula (2), —COO— is preferred as X. A single bond or a linear or branched alkylene group having 1 to 20 carbon atoms is preferred as $A^1$, and a single bond or —OCO is preferred as $B^1$. It is also preferred that $A^1$ and $B^1$ represent a poly(alkyleneoxy)carbonyl group together with each other. As Y, is preferred a hydrogen atom, a phenyl or naphthyl group substituted by 1 to 3 carboxyl groups, a $C_{1-4}$ alkyl or alkenyl group substituted by 1 or 2 carboxyl groups, a naphthalenedicarboxylic acid anhydride residue or a phthalic acid anhydride residue.

Preferable other examples of the polymer (A) include homopolymers and copolymers having a structural unit represented by the following formula (3):

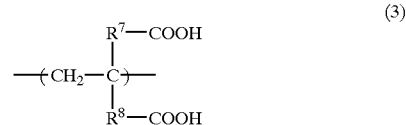

wherein $R^7$ and $R^8$ are the same or different from each other and are independently a single bond or an organic group which may be substituted.

In the formula (3), it is particularly preferred that $R^7$ and $R^8$ are the same or different from each other and are independently a single bond or a $C_{1-20}$ alkylene group.

Examples of another monomer in the case where the polymer (A) is a copolymer having the structural unit of the formula described above include other monomers than the carboxyl and carbonyloxycarbonyl groups, which may have a functional group. For example, one or more of (meth) acrylates ($C_1$ to $C_{18}$ alkyl esters, $C_2$ to $C_{18}$ alkenyl esters, cycloalkyl esters, alkoxyalkyl esters, cyclic ether esters, phenoxyalkyl esters, dialkylaminoalkyl esters, polyoxyalkylene esters, etc.), (meth)acrylamides (amides, alkylamides, dialkylamides, etc.), aliphatic vinyls ($C_1$ to $C_{24}$ aliphatic vinyls, etc.), styrene monomers (styrene, alkylstyrene monomers, etc.), vinylpyridine monomers, vinylpyrrolidone monomers and maleimides (N-phenyl- maleimide, etc.) may also be used. Examples of monomers having a sulfonic acid residue include 2-acrylamide-2-methylpropanesulfonic acid and sodium styrenesulfonate. These other monomers are preferably used in a proportion of about 2 to 10% of the whole monomer.

The weight average molecular weight of the polymer (A) is 10,000 to 5,000,000, preferably 10,000 to 1,000,000, more preferably 15,000 to 500,000, most preferably 20,000 to 200,000. If the weight average molecular weight is lower than 10,000, the strength of a coating formed on teeth becomes low, and so its durability is insufficient. If the weight average molecular weight is higher than 5,000,000, such a polymer is hard to be dissolved in a solvent, and so any tooth coating composition is hard to be prepared.

The polymer (A) must have such characteristics that the solubility in 100 g of absolute ethanol is 1 g or higher at 20° C. and the solubility in 100 g of water is 10 g or lower at 20° C. If the solubility in ethanol is lower than 1 g, any tooth coating composition is hard to be prepared. If the solubility in water exceeds 10 g, the water resistance of such a polymer is low, and so the durability of the resulting coating becomes insufficient. No upper limit is imposed on the solubility in absolute ethanol so far as it is 1 g or higher. On the other hand, the polymer (A) may be insoluble in water so far as the solubility in water is 10 g or lower. Incidentally, the solubility of a polymer in absolute ethanol is determined in the following manner. The polymer (10 g) is added to absolute ethanol (100 g), and the mixture is stirred at 20° C. for 1 hour. The remaining polymer is then separated by filtration to measure its weight, thereby finding an amount of the polymer dissolved from a difference between the weight of the polymer before the dissolution and the weight of the remaining polymer. The solubility of the calcium salt of the polymer is determined in the following manner. Calcium chloride in an equimolar amount to a carboxyl and/or phosphoric group in the polymer is added to a polymer solution prepared in the above-described manner. The mixture is then stirred at 20° C. for 1 hour. Thereafter, a polymer precipitated is separated by filtration to measure its weight, thereby finding an amount of the polymer dissolved from a difference between the weight of the polymer before the dissolution and the weight of the polymer precipitated.

The polymer (A) is preferably such that its calcium salt has a solubility of 2 g or lower in 100 g of water at 20° C. and a solubility of 1 g or higher in 100 g of absolute ethanol at 20° C. When the tooth coating composition according to the present invention is applied to teeth, the polymer (A) reacts with calcium on the surfaces of the teeth or in saliva in the mouth to form a salt. Accordingly, the polymer may preferably be a water-soluble polymer having a solubility of 10 g or lower so far as it forms a salt with calcium to lower its water-solubility, thereby improving its water resistance, because its durability in the mouth is enhanced. A more preferable solubility of the calcium salt in 100 g of water at 20° C. is 0.5 g or lower, while a more preferable solubility in absolute ethanol 100 g at 20° C. is 2 g or higher. Moderate durability and removability when intended to be removed can be imparted to the coating agent according to the present invention as far as the polymer (A) has such solubility characteristics.

The acid value of the polymer (A) is preferably at least 0.1, particularly 0.1 to 700 from the viewpoints of adhesive property to teeth and durability of a coating.

The polymer (A) is preferably incorporated in a proportion of 1 to 70% by weight (hereinafter indicated merely by "%"), particularly 5 to 40% in the composition according to the present invention.

The composition according to the present invention is provided in the form of a dispersion by incorporating (B) water or an alcohol having 1 to 5 carbon atoms into the polymer (A). The alcohol having 1 to 5 carbon atoms is a linear or branched, saturated alcohol. Among others, ethanol and isopropyl alcohol are preferred, with ethanol being particularly preferred. Two or more components selected from water and these alcohols may also be used in combination. Water or these alcohols are preferably incorporated in a proportion of 30 to 98%, particularly 50 to 95% based of the total weight of the composition.

Into the composition according to the present invention, is preferably incorporated an inorganic pigment such as mica titanium, titanium oxide or powder of shell, or an organic pigment such as fish scale guanine for the purpose of imparting aesthetic property and gloss (luster) to teeth.

With respect to mica titanium used in the present invention, that having an average particle diameter of 1 to 200 μm is preferably used from the viewpoint of aesthetic property and gloss (luster). That having an average particle diameter of 10 to 100 μm is particularly preferred. With respect to titanium oxide, that having an average particle diameter of 5 nm to 5 μm is preferably used by the same reason as described above. That having an average particle diameter of 10 nm to 0.5 μm is particularly preferred. Mica titanium and titanium oxide may be used either singly or in combination.

The amount of these powders added to the composition according to the present invention is preferably 0.1 to 10%, more preferably 0.2 to 5% from the viewpoints of gloss-imparting property and even coating property.

A blending ratio of the polymer (A) to mica titanium and/or titanium oxide is preferably 1:0.01 to 1:1 in terms of weight ratio from the viewpoints of gloss-imparting property and even coating property.

Into the composition according to the present invention, may be further added various kinds of powder. For example, a-quartz, silica, alumina, hydroxyapatite, calcium carbonate, fluoroaluminosilicate glass, barium sulfate, zirconia, glass, ultrafine silica, and organic composite powder containing an organic component and an inorganic component may be used. Powder of polymers such as polymethyl methacrylate, copolymers of methyl methacrylate and a crosslinkable monomer, polystyrene and polyvinyl chloride may also be added as needed.

Into the composition according to the present invention, may be further incorporated various kinds of publicly known ingredients, for example, dentine reinforcing agents such as sodium monofluorophosphate, tin fluoride and sodium fluoride; germicides; pH adjusters, enzymes; anti-inflammatory agents and blood circulation-facilitating agents; sweeteners; colorants and coloring matter; and perfume bases.

The composition according to the present invention can be provided in accordance with a method known per se in the art, for example, by mixing the polymer (A) and the component (B), and optionally the above-described pigment, a thickener such as ethyl cellulose, hydroxypropyl cellulose or carboxyvinyl polymer, and the like.

The composition according to the present invention can be caused to adhere to teeth by applying it to the teeth in accordance with a method known per se in the art and evaporating a solvent component. The tooth coating agent adhered to the teeth can be easily removed by means of ethanol or the like.

The viscosity of the composition according to the present invention upon its application to teeth is preferably 2 to 500 mPa.s, particularly 5 to 200 mPa.s. If the viscosity is lower than 2 mPa.s, there is a possibility that the composition may drip in or out the mouth. If the viscosity is higher than 500 mPa.s on the other hand, the spreading of the composition becomes poor, and so it is difficult to evenly apply the composition to the surfaces of teeth. The viscosity of the composition as used herein means a value measured by a Brookfield type viscometer.

EXAMPLES

Example 1

After a reaction vessel was charged with dimethoxyethane (146.0 g), ethyl methacrylate (18.9 g), isopropyl methacrylate (21.6 g) and 4-methacryloyloxy trimellitic anhydride (represented by the following formula (a-1); 9.5 g), nitrogen gas was introduced for 30 minutes at a flow rate of 1.5 L/min into the vessel. After the resultant monomer solution was then heated to 60° C. with stirring in a hot water bath, 2,2'-azobis(2,4-dimethyl valeronitrile) (0.44 g) was dissolved in dimethoxyethane (12.5 g), and the resultant solution was added to the monomer solution over 30 minutes. Thereafter, the monomer solution was polymerized at 60° C. for 4 hours and at 75° C. for 4 hours. A polymer formed was precipitated with a 2:1 (weight ratio) mixture (5 L) of ethanol/water to purify the polymer (twice), and then dried at 60° C. for 6 hours. The thus-obtained copolymer had a weight average molecular weight (in terms of polystyrene as measured by GPC; the same shall apply hereinafter) of 72,000 and an acid value of 81 KOH mg/g.

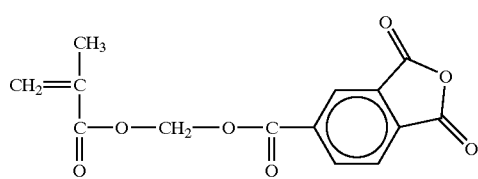

(a-1)

This polymer (15 g), titanium oxide (1 g), mica titanium (1 g) and ethanol (88 g) were mixed with one another to obtain a tooth coating composition 1.

Example 2

Dimethoxyethane (146 g), the following compound (a-2) (6.0 g), methyl methacrylate (15.0 g), t-butyl methacrylate (29.0 g) and 2,2'-azobis(2,4-dimethyl valeronitrile) (0.50 g) were used to obtain a copolymer having a molecular weight of 104,000 and an acid value of 39 in a similar manner to Example 1.

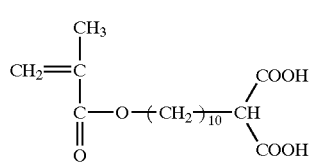

(a-2)

This polymer (15 g), titanium oxide (1 g), mica titanium (1 g) and ethanol (88 g) were mixed with one another to obtain a tooth coating composition 2.

Example 3

Dimethoxyethane (146 g), the following compound (a-3) (2.6 g), 2-ethylhexyl methacrylate (20.6 g), ethyl methacrylate (26.8 g) and 2,2'-azobis(2,4-dimethyl valeronitrile) (0.45 g) were used to obtain a polymer having a molecular weight of 90,000 and an acid value of 15 in a similar manner to Example 1.

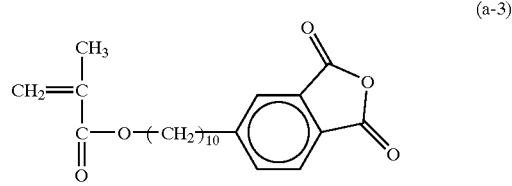

(a-3)

This polymer (15 g), titanium oxide (1 g), mica titanium (1 g) and ethanol (88 g) were mixed with one another to obtain a tooth coating composition 3.

Example 4

Dimethoxyethane (146 g), the following compound (a-4) (9.6 g), isopropyl methacrylate (21.6 g), ethyl methacrylate (18.8 g) and 2,2'-azobis(2,4-dimethyl valeronitrile) (0.45 g) were used to obtain a polymer having a molecular weight of 72,000 and an acid value of 79 in a similar manner to Example 1.

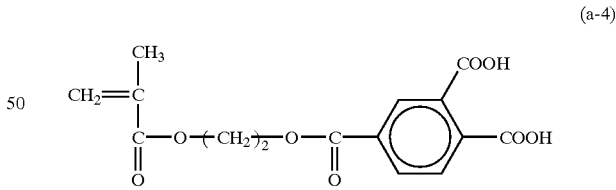

(a-4)

This polymer (15 g), titanium oxide (1 g), mica titanium (1 g) and ethanol (88 g) were mixed with one another to obtain a tooth coating composition 4.

Example 5

Dimethoxyethane (146 g), the following compound (a-5) (23.9 g), ethyl methacrylate (9.8 g), t-butyl methacrylate (16.3 g) and 2,2'-azobis(2,4-dimethyl valeronitrile) (0.28 g) were used to obtain a polymer having a molecular weight of 124,000 and an acid value of 90 in a similar manner to Example 1.

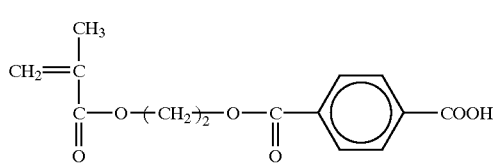
(a-5)

This polymer (15 g), titanium oxide (1 g), mica titanium (1 g) and ethanol (88 g) were mixed with one another to obtain a tooth coating composition 5.

Example 6

Dimethoxyethane (146 g), the following compound (a-6) (18.1 g), t-butyl methacrylate (31.9 g) and 2,2'-azobis(2,4-dimethylvaleronitrile) (0.40 g) were used to obtain a polymer having a molecular weight of 49,000 and an acid value of 119 in a similar manner to Example 1.

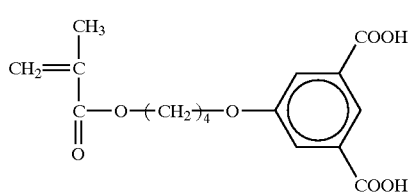
(a-6)

This polymer (15 g), titanium oxide (1 g), mica titanium (1 g) and ethanol (88 g) were mixed with one another to obtain a tooth coating composition 6.

Example 7

Dimethoxyethane (146 g), the following compound (a-7) (18.1 g), ethyl methacrylate (31.9 g) and 2,2'-azobis(2,4-dimethylvaleronitrile) (0.39 g) were used to obtain a polymer having a molecular weight of 85,000 and an acid value of 160 in a similar manner to Example 1.

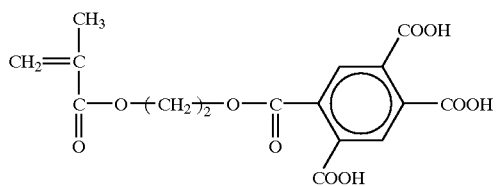
(a-7)

This polymer (15 g),, titanium oxide (1 g), mica titanium (1 g) and ethanol (88 g) were mixed with one another to obtain a tooth coating composition 7.

Example 8

Ethanol (146 g), the following compound (a-8) (12.7 g), ethyl methacrylate (24.5 g), N,N-dimethylacrylamide (12.8 g) and 2,2'-azobis(2,4-dimethylvaleronitrile) (0.50 g) were used to obtain a polymer having a molecular weight of 63,000 and an acid value of 94 in a similar manner to Example 1.

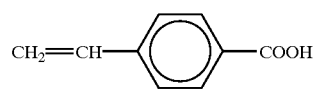
(a-8)

This polymer (15 g), titanium oxide (1 g), mica titanium (1 g) and ethanol (88 g) were mixed with one another to obtain a tooth coating composition 8.

Example 9

Dimethoxyethane (146 g), the following compound (a-9) (19.1 g), t-butyl methacrylate (31.9 g) and 2,2'-azobis(2,4-dimethylvaleronitrile) (0.50 g) were used to obtain a polymer having a molecular weight of 104,000 and an acid value of 105 in a similar manner to Example 1.

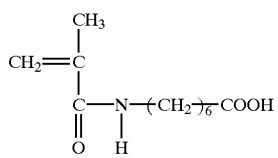
(a-9)

This polymer (15 g), titanium oxide (1 g), mica titanium (1 g) and ethanol (88 g) were mixed with one another to obtain a tooth coating composition 8.

Example 10

Dimethoxyethane (146 g), the following compound (a-10) (22.6 g), ethyl methacrylate (12.2 g), t-butyl methacrylate (15.2 g) and 2,2'-azobis(2,4-dimethyl valeronitrile) (0.40 g) were used to obtain a polymer having a molecular weight of 71,000 and an acid value of 120 in a similar manner to Example 1.

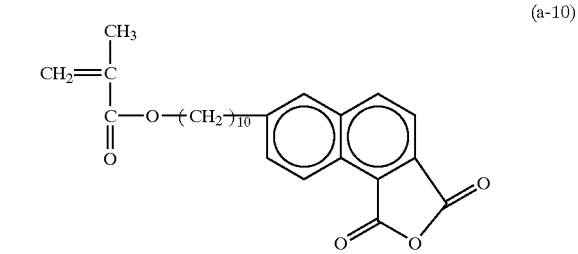
(a-10)

This polymer (15 g), titanium oxide (1 g), mica titanium (1 g) and ethanol (88 g) were mixed with one another to obtain a tooth coating composition 10.

Example 11

Dimethoxyethane (146 g), the following compound (a-11) (20.5 g), ethyl methacrylate (24.8 g), N,N-dimethylacrylamide (4.7 g) and 2,2'-azobis(2,4-dimethyl valeronitrile) (0.40 g) were used to obtain a polymer having a molecular weight of 89,000 and an acid value of 101 in a similar manner to Example 1.

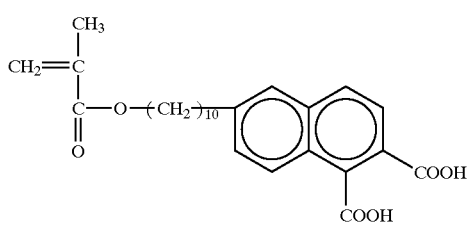

This polymer (15 g), titanium oxide (1 g), mica titanium (1 g) and ethanol (88 g) were mixed with one another to obtain a tooth coating composition 11.

Example 12

Ethanol (146 g), the following compound (a-12) (19.8 g), t-butyl methacrylate (30.2 g) and 2,2'-azobis(2,4-dimethylvaleronitrile) (0.36 g) were used to obtain a polymer having a molecular weight of 67,000 and an acid value of 103 in a similar manner to Example 1.

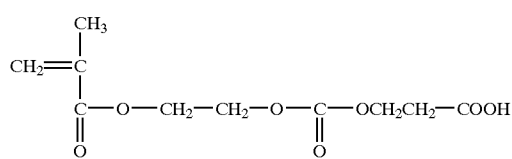

This polymer (15 g), titanium oxide (1 g), mica titanium (1 g) and ethanol (88 g) were mixed with one another to obtain a tooth coating composition 12.

Example 13

Dimethoxyethane (146 g), the following compound (a-13) (25.3 g), isopropyl methacrylate (24.7 g) and 2,2'-azobis(2, 4-dimethylvaleronitrile) (0.32 g) were used to obtain a polymer having a molecular weight of 57,000 and an acid value of 180. in a similar manner to Example 1.

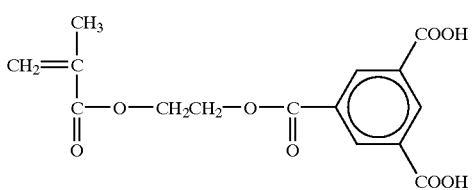

This polymer (15 g), titanium oxide (1 g), mica titanium (1 g) and ethanol (88 g) were mixed with one another to obtain a tooth coating composition 13.

Example 14

Dimethoxyethane (146 g), the compound (a-2) (6.0 g) used in Example 2, methyl methacrylate (13.0 g), t-butyl methacrylate (29.0 g), sodium styrenesulfonate (11.5 g) and 2,21-azobis(2,4-dimethylvaleronitrile) (0.50 g) were used to obtain a polymer having a molecular weight of 104,000 and an acid value of 39 in a similar manner to Example 1.

This polymer (15 g), titanium oxide (1 g), mica titanium (1 g) and ethanol (88 g) were mixed with one another to obtain a tooth coating composition 14.

Comparative Example 1

Dimethoxyethane (146 g), the compound (a-2) (6.0 g) used in Example 2, methyl methacrylate (15.0 g), t-butyl methacrylate (29.0 g), 1-dodecanethiol (2 g) and 2,2'-azobis (2,4-dimethylvaleronitrile) (0.50 g) were used to obtain a polymer having a molecular weight of 8,000 and an acid value of 35 in a similar manner to Example 1.

This polymer (15 g), titanium oxide (1 g), mica titanium (1 g) and ethanol (88 g) were mixed with one another to obtain a comparative tooth coating composition 1.

Comparative Example 2

Dimethoxyethane (146 g), ethyl methacrylate (23.0 g), t-butyl methacrylate (27.0 g) and 2,2'-azobis(2,4-dimethylvaleronitrile) (0.50 g) were used to obtain a polymer having a molecular weight of 89,000 and an acid value of 0 in a similar manner to Example 1.

This polymer (15 g), titanium oxide (1 g), mica titanium (1 g) and ethanol (88 g) were mixed with one another to obtain a comparative tooth coating composition 2.

Test Example 1

A test was performed on peeling resistance upon eating and drinking. Panelists were divided into groups consisting of 7 members. A tooth coating sample was applied to the whole surfaces of 6 foreteeth in the upper jaw of each panelist at 9 a.m. to take a photograph of the foreteeth. The panelist was got to drink water (200 ml) at 10 a.m., eat and drink a commercially available hamburger, a commercially available fried chicken, a lettuce and tomato salad (100 g), a steamed potato and a commercially available oolong tea (200 ml) at noon and further drink water (200 ml) at 3 p.m. A photograph of the foreteeth was then taken at 6 p.m. The photograph was compared with the photograph taken at 9 a.m., thereby judging the degree of the tooth coating composition remaining on the foreteeth in accordance with the following standard. The results are shown in Table 1. In Table 1, are shown solubilities of the polymers used and the calcium salts thereof in solvents at 20° C.

Evaluation Standard:

Score 3: No peeling was observed;

Score 2: Peeling was observed only at the tips of the teeth;

Score 1: Peeling was observed at a portion smaller than a quarter of the teeth

Score 1: Peeling was observed at a portion not smaller than a quarter of the teeth.

|  | Solubility of polymer | | Solubility of calcium salt | | |
| --- | --- | --- | --- | --- | --- |
|  | Solubility in EtOH | Solubility in water | Solubility in EtOH | Solubility in water | Test score |
| Ex. 1 | ≧10 g | ≦0.1 g | ≧10 g | ≦0.1 g | 2.5 |
| Ex. 2 | ≧10 g | ≦0.1 g | ≧10 g | ≦0.1 g | 2.7 |
| Ex. 3 | ≧10 g | ≦0.1 g | ≧10 g | ≦0.1 g | 2.4 |
| Ex. 4 | ≧10 g | ≦0.1 g | 2.3 | ≦0.1 g | 2.4 |
| Ex. 5 | ≧10 g | ≦0.1 g | 8.2 | ≦0.1 g | 2.3 |
| Ex. 6 | ≧10 g | ≦0.1 g | 3.5 | ≦0.1 g | 2.3 |
| Ex. 7 | ≧10 g | ≦0.1 g | 2.1 | ≦0.1 g | 2.1 |
| Ex. 8 | ≧10 g | ≦0.1 g | 6.7 | ≦0.1 g | 2 |
| Ex. 9 | ≧10 g | ≦0.1 g | 5.8 | ≦0.1 g | 2.4 |
| Ex. 10 | ≧10 g | ≦0.1 g | 6.1 | ≦0.1 g | 2.1 |
| Ex. 11 | ≧10 g | ≦0.1 g | 4.2 | ≦0.1 g | 2.3 |
| Ex. 12 | ≧10 g | ≦0.1 g | 7.5 | ≦0.1 g | 2.4 |

-continued

| | Solubility of polymer | | Solubility of calcium salt | | |
|---|---|---|---|---|---|
| | Solubility in EtOH | Solubility in water | Solubility in EtOH | Solubility in water | Test score |
| Ex. 13 | ≧10 g | ≦0.1 g | 3.2 | ≦0.1 g | 2.6 |
| Comp. Ex. 1 | ≧10 g | ≦0.1 g | ≦10 g | ≦0.1 g | 0.8 |
| Comp. Ex. 2 | ≧10 g | ≦0.1 g | No salt was formed | ≦0.1 g | 0.2 |

From Table 1, it was proved that the tooth coating compositions according to the present invention are hard to be peeled even when eaten and drunk.

Test Example 2

Bovine teeth were etched with phosphoric acid and then coated with Panavia EX (product of Kuraray Co., Ltd.), which is a dental adhesive, in accordance with a method known per se in the art. Bovine teeth were also coated with each of the compositions according to Examples 1 to 14 in the same manner as described above. Thereafter, the thus-coated teeth were immersed at 36° C. for 24 hours in artificial saliva (Salivate, product of Teijin Limited) and then subjected to a removal test with absorbent cotton soaked with ethanol. The dental adhesive was not removed with ethanol at all, but all the tooth coating compositions 1 to 14 were able to be almost completely removed.

INDUSTRIAL APPLICABILITY

According to the present invention, there can be provided tooth coating compositions having such moderate adhesive strength that the coating is not easily peeled by eating and drinking, but can be easily removed if necessary.

What is claimed is:

1. A teeth coating composition comprising (A) a polymer having one or more carboxyl or carbonyloxycarbonyl groups in its molecule, a weight average molecular weight of 10,000 to 5,000,000, a solubility of 1 g or higher in 100 g of absolute ethanol at 20° C. and a solubility of 10 g or lower in 100 g of water at 20° C., and (B) water or an alcohol having 1 to 5 carbon atoms, or a mixture of said alcohols or a mixture of water and said alcohol(s), wherein the polymer (A) is selected from the group consisting of homopolymers and copolymers having a structural unit represented by the following formula (2):

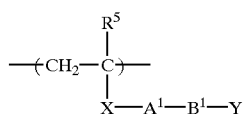

(2)

wherein $R^5$ is a hydrogen atom or a hydrocarbon group which may be substituted by a halogen atom, X is —COO— or —CON($R^6$)—, in which $R^6$ is a hydrogen atom or an alkyl group, $A^1$ is a single bond or a hydrocarbon group which may be substituted by a halogen atom, $B^1$ is a single bond, —OCO—, —COO—, —O—, —NHCO— or —CONH—, or may be present a polyalkyleneoxy or poly(alkyleneoxy)carbonyl group together with $A^1$, and Y is a hydrogen atom, a carboxyl group, an aryl group substituted by 1 to 3 carboxyl groups, an alkyl or alkenyl group substituted by 1 or 2 carboxyl groups, or a carbonyloxycarbonyl-substituted aryl group, with the proviso that the structural unit wherein $R^5$ is a hydrogen atom, X is —COO—, $A^1$ is a single bond, $B^1$ is a single bond, and Y is a hydrogen atom, is excluded.

2. The composition according to claim 1, wherein the acid value of the polymer (A) is at least 0.1.

3. The composition according to claim 1, which further comprises a pigment selected from mica titanium, titanium oxide, fish scale guanine and powder of shell.

4. The composition according to claim 1, wherein the viscosity of the composition is 2 to 500 mPa.s.

5. The composition according to claim 1, wherein in formula (2), X is —COO—, $A^1$ is a single bond or a linear or branched alkylene group having 1 to 20 carbon atoms, $B^1$ is a single bond or —OCO—, or $A^1$ and $B^1$ represent a poly(alkyleneoxy)carbonyl group together with each other, and Y is a hydrogen atom, a phenyl or naphthyl group substituted by 1 to 3 carboxyl groups, a $C_{1-4}$ alkyl or alkenyl group substituted by 1 or 2 carboxyl groups, a naphthalene-dicarboxylic acid anhydride residue or a phthalic acid anhydride residue.

6. A teeth coating composition comprising (A) a polymer having one or more carboxyl or carbonyloxycarbonyl groups in its molecule, a weight average molecular weight of 10,000 to 5,000,000, a solubility of 1 g or higher in 100 g of absolute ethanol at 20° C. and a solubility of 10 g or lower in 100 g of water at 20° C., and (B) water or an alcohol having 1 to 5 carbon atoms, or a mixture of said alcohols or a mixture of water and said alcohol(s), wherein the polymer (A) is selected from the group consisting of homopolymers and copolymers having a structural unit represented by the following formula (3):

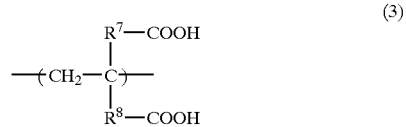

(3)

wherein $R^7$ and $R^8$ are the same or different from each other and are independently a single bond or an organic group which may be substituted.

7. The composition according to claim 6, wherein in formula (3), $R^7$ and $R^8$ are the same or different from each other and are independently a single bond or a $C_{1-20}$ alkylene group.

8. The composition according to claim 6, wherein the acid value of the polymer (A) is at least 0.1.

9. The composition according to claim 6, which further comprises a pigment selected from mica titanium, titanium oxide, fish scale guanine and powder of shell.

10. The composition according to claim 6, wherein the viscosity of the composition is 2 to 500 mPa.s.

11. A teeth coating composition comprising (A) a polymer having one or more carboxyl or carbonyloxycarbonyl groups in its molecule, a weight average molecular weight of 10,000 to 5,000,000, a solubility of 1 g or higher in 100 g of absolute ethanol at 20° C. and a solubility of 10 g or lower in 100 g of water at 20° C., and (B) water or an alcohol having 1 to 5 carbon atoms, or a mixture of said alcohols or a mixture of water and said alcohol(s), wherein the polymer (A) contains a structural unit obtained from one of the compounds of the following formulas (a-1) through (a-13):

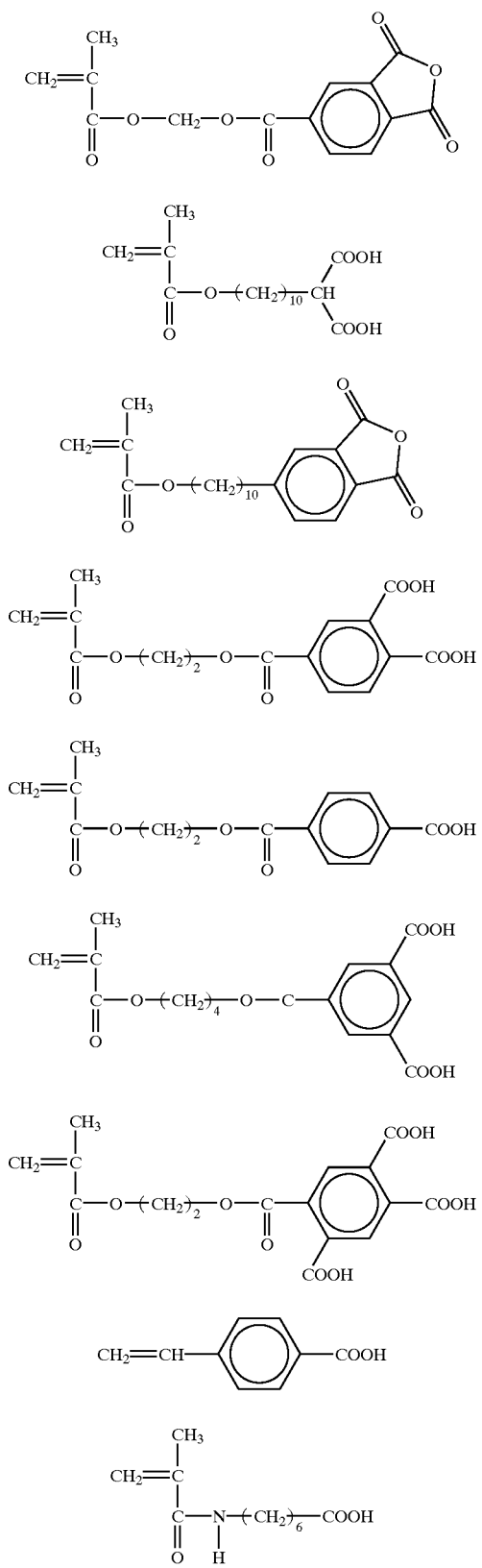
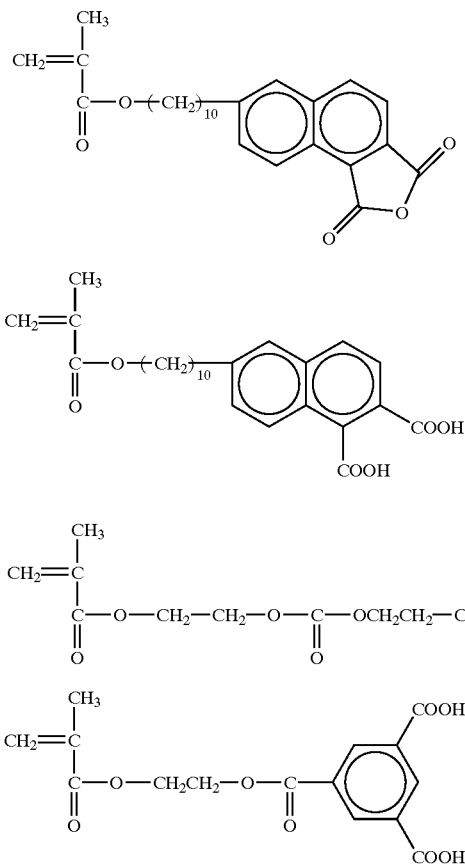

12. The composition according to claim 11, wherein the acid value of the polymer (A) is at least 0.1.

13. The composition according to claim 11, which further comprises a pigment selected from mica titanium, titanium oxide, fish scale guanine and powder of shell.

14. The composition according to claim 11, wherein the viscosity of the composition is 2 to 500 mPa.s.

15. A method for coating teeth, which comprises applying to teeth, a teeth coating composition comprising (A) a polymer having one or more carboxyl or carbonyloxycarbonyl groups in its molecule, a weight average molecular weight of 10,000 to 5,000,000, a solubility of 1 g or higher in 100 g of absolute ethanol at 20° C. and a solubility of 10 g or lower in 100 g of water at 20° C., and (B) water or an alcohol having 1 to 5 carbon atoms, or a mixture of said alcohols or a mixture of water and said alcohol(s), wherein a calcium salt of the polymer (A) has a solubility of 2 g or lower in 100 g of water at 20° C. and a solubility of 1 g or higher in 100 g of absolute ethanol at 20° C., evaporating component (B), and thereby adhering component (A) to teeth.

* * * * *

UNITED STATES PATENT AND TRADEMARK OFFICE
CERTIFICATE OF CORRECTION

PATENT NO.    : 6,491,898 B1
DATED         : December 10, 2002
INVENTOR(S)   : Yamagishi et al.

It is certified that error appears in the above-identified patent and that said Letters Patent is hereby corrected as shown below:

<u>Title page,</u>
Insert Item [30], Foreign Application Priority Data

--      [30]    Foreign Application Priority Data

Sep. 19, 1997    (JP) .................................. 9-255026 --

Signed and Sealed this

Thirteenth Day of May, 2003

JAMES E. ROGAN
*Director of the United States Patent and Trademark Office*